United States Patent [19]

Sekimoto et al.

[11] Patent Number: 4,485,098

[45] Date of Patent: Nov. 27, 1984

[54] METHOD FOR PROMOTING HEALING OF WOUND AND LOWERING BLOOD LEVEL OF CREATINE PHOSPHOKINASE

[75] Inventors: Kunitoshi Sekimoto, Sagamihara; Yoneji Mamiya, Hiratuka; Tadashi Ishikawa, Sagamihara, all of Japan

[73] Assignee: Nihon Nosan Kogyo K.K., Yokohama, Japan

[21] Appl. No.: 561,059

[22] Filed: Dec. 13, 1983

[30] Foreign Application Priority Data

Dec. 22, 1982 [JP] Japan ................................ 57-223692

[51] Int. Cl.$^3$ ............................................. A61K 35/54
[52] U.S. Cl. ...................................... 424/105; 424/95
[58] Field of Search .................................. 424/95, 105

[56] References Cited

PUBLICATIONS

Katamine et al., Chem. Abst., vol. 96, (1982), p. 5417h.
Katamine, Chem. Abst., vol. 96, (1982), p. 33853r.

*Primary Examiner*—Sam Rosen
*Attorney, Agent, or Firm*—Martin Smolowitz

[57] ABSTRACT

A method for promoting healing of wounds or lowering the amount of creatine phosphokinase in the blood during muscular exercise by using iodine-enriched eggs containing iodine in an amount of about 300 to 5,000 μg per egg. The iodine-enriched eggs can be obtained by giving an iodine compound and/or seaweed to egg-laying hens. Intake of the iodine-enriched egg is determined so that the iodine dose will be about 300 to 1,500 μg per day.

9 Claims, No Drawings

METHOD FOR PROMOTING HEALING OF WOUND AND LOWERING BLOOD LEVEL OF CREATINE PHOSPHOKINASE

This invention relates to a novel method for promoting healing of wounds and preventing muscular troubles.

Retinolic acid, allantoin, asiatocoside as a component of umbelliferous plants, and zinc are known as typical substances capable of promoting healing of wounds, but none of these medicative substances is fully satisfactory in ther effect. Thus, in the attempt at healing wounds, devising and application of a safe and effective method for promoting healing of wounds by oral intake of a medicative substance in addition to a surgical treatment such as suture has been desired.

Under these circumstances, the present inventors took note of and studied the relation between nutrition in every day dining, especially protein nutrition, and healing of wounds and, as a result, found quite surprisingly that an egg having a high content of iodine or iodine-enriched egg, has an effect of promoting healing of wounds as well as preventing muscular troubles, and this finding has led to the present invention.

According to the investigation by the present inventors, there is no report elucidating or suggesting the fact that iodine itself or an iodine-enriched egg is effective in promoting healing of wounds as well as preventing muscular troubles. Therefore, the present invention may be said to be a pioneer invention.

Hereinafter, the invention will be described in detail.

The iodine-enriched egg used in the method of this invention can be obtained usually in the following way. An iodine compound such as calcium iodate, potassium iodate, potassium iodide, sodium iodide, copper iodide, idothymol, calcium iodobehenate, diiodosalicyclic acid or calcium periodate and/or seaweed such as tangle or kelp, either in the raw form or processed, is mixed in a feed by at least a given amount, and the mixed feed is given to egg-laying poultry so that the iodine content in the egg is increased. Considering the health of the egg-laying poultry, transfer rate of iodine into egg and other factors, calcium iodate is the most desirable iodine compound. It is even more desirable to apply such a compound together with seaweed such as kelp. The amount of iodine dosed to the egg-laying poultry varies depending on the species of the poultry such as domestic fowl (hen) and quail, but usually said compound and/or seaweed are added so that the iodine content in the feed will be 50 to 2,500 ppm, preferably 50 to 150 ppm. It is especially desirable to mix said compound and seaweed such that the iodine derived from the iodine compound will be contained in an amount of 40 to 100 ppm and the one derived from the seaweed 10 to 50 ppm.

The poultry fed with a feed with a high content of said iodine compound or iodine begin to lay the desired iodine-enriched eggs about one week after the start of the feeding. In the case of egg-laying hens for instance, when they are fed with a feed containing about 50 ppm of iodine, they lay eggs containing about 300 μg of iodine per egg. When they are fed with a feed with about 100 ppm of iodine, they lay eggs containing about 600 to 800 μg of iodine per egg. Also, feeding with a feed containing about 2,500 ppm of iodine allows laying of eggs with an iodine content of about 4,000 to 5,000 μg per egg.

The obtained iodine-enriched eggs may be used in the form as they are for the purpose of this invention. Also the yolk may be separated from the egg in order to use the yolk alone as the effective substance in the method of this invention, as the yolk portion is especially effectual. The iodine-enriched egg or the yolk separated therefrom may be used after suitable processing, for example, drying, concentration, powdering or granulation. They may further be used in the form of a tablet, powder, extract, syrup, emulsion or such by mixing various kinds of excipient, binder and/or other additives.

The iodine-enriched eggs used in the method of this invention have no problem with safety because the egg-laying poultry's body serves as a vital filter. It is recommended to take such eggs usually at meals or before or after meals in a given amount every day.

According to this invention, by taking said eggs such that iodine will be dosed in an amount of usually 300 to 1,500 μg per day for an adult, it is possible to promote healing of wounds or to prevent muscular troubles. More specifically, for actual intake per day, it is suggested to take one to three eggs each containing about 300 to 1,500 μg of iodine, everyday. In case the iodine-enriched egg or its yolk is granulated, a suitable amount of such granulated product may be taken according to the iodine content in the product so that approximately 300 to 1,500 μg of iodine will be ingested per day.

Thus, continuous take of said iodine-enriched egg or a preparation formed by granulating or otherwise working such egg proves helpful in promoting healing of wounds, and especially in the case of an operative wound, if the iodine-enriched egg or a worked preparation thereof according to this invention is taken before the operation, healing of the wound is markedly promoted. A sportsman or a person who takes excessive exercise tends to suffer from a subcutaneous severance of muscle or a torn muscle, but such muscular troubles can be prevented by continuously taking the iodine-enriched egg according to this invention.

The results of animal experiments and clinical tests on the promotion of healing of wounds by the method of this invention are described below.

EXPERIMENT 1

Male Wistar rats were divided into two groups of six, one group being a test group and the other a control group. The rats of the test group were fed with a solid feed prepared by mixing 5% of powdered iodine-enriched egg obtained according to the method of Example 2 in a commercially available rat feed. The rats of the control group were fed with a solid feed prepared by mixing 5% of ordinary powdered egg in said commercially available rat feed. At the 20th day from start of feeding with said feed, an incised wound of 4 cm in length was made along a median line on the back of each of said rats with a body weight of around 150 g under anesthesia. After seven days, each rat was again anesthesized to avulse the skin of said incised wound portion, and a 1 cm skin piece was cut transversely to the wound line with a razor to make a specimen. The tension (g/cm) required for cutting said skin piece of the wound portion was recorded by a rheometer (tension meter) and given as an indication of the degree of promoting healing of the wound. The results are shown in Table 1, from which it is evident that the method of this invention is effective in promoting healing of wound.

TABLE 1

| Rat No. | Test Group | (Unit: g/cm) Control Group |
|---|---|---|
| 1 | 440.0 | 236.7 |
| 2 | 378.9 | 353.3 |
| 3 | 451.7 | 193.3 |
| 4 | 261.7 | 206.7 |
| 5 | 406.4 | 315.0 |
| 6 | 351.4 | 276.7 |
| average | 381.7 | 263.6 |

EXPERIMENT 2

Male Wistar rats were divided into three groups, that is, a test group, control group and a comparative group, each group consisting of 7 rats. The rats of the test group were fed with a feed prepared by mixing 5% of powdered iodine-enriched egg of Example 2 in a marketed rat feed, while the rats of both control and comparative groups were fed with a feed prepared by mixing 5% of ordinary powdered egg in the marketed rat feed. 20 days after the start of feeding with said feed, an incised wound was made in the same way as in Experiment 1 on the back of each of the rats with a body weight of around 150 g and, for a period of 7 days thereafter, the rats of the test group and the comparative group were given intraperitoneal injections of a solution prepared by dissolving $\beta$-aminopropionitrile ($\beta$-APN) in a physiological saline solution so that said compound wounds have a concentration of 40 mg per 100 of rat body weight. The rats of the control group had intraperitoneal injections of a physiological saline solution alone. Seven days after making the wound, the tensile strength of the skin at the wound region of each rat was measured in the same way as in Experiment 1. The results are shown in Table 2.

TABLE 2

| Rat No. | Test Group | Comparative Group | (unit: g/cm) Control Group |
|---|---|---|---|
| 1 | 343.3 | 268.3 | 371.7 |
| 2 | 213.3 | 185.0 | 200.0 |
| 3 | 276.7 | 263.3 | 321.7 |
| 4 | 321.7 | 301.7 | 306.7 |
| 5 | 150.0 | 195.0 | 250.0 |
| 6 | 266.7 | 235.0 | 276.7 |
| 7 | 293.3 | 231.7 | 341.7 |
| average | 266.4 | 240.0 | 295.5 |

As a result of $\beta$-APN administration, the rats of the comparative group showed a statistically significant drop in tensile strength of the skin in comparison with those of the control group. In the case of the rats of the test group, although a drop of tensile strength was seen, the degree of such a drop was very small, presenting substantially no significant difference from those of the control group. Thus, the method of this invention was found to be effective in antagonizing the inhibitory action of $\beta$APN against crosslinking of collagen, that is, an effect of promoting healing of wounds.

CLINICAL TEST 1

32 patients of gastric ulcer or tumor, who needed a surgical operation, were allowed to take the iodine-enriched eggs obtained according to the method of Example 1 everyday on a one-egg-a-day basis for a period of 2 to 4 weeks before undergoing an operation. After the operation, when they became able to take ordinary meals, they were given the iodine-enriched eggs in the same way as above. Ordinarily, the stitches are taken out 7 days after the operation, but the patients under test who had the iodine-enriched eggs showed a good state of tension at the lip of the wound and a favorable local blood circulation, and 22 patients could have their stitches taken out five days after the operation and 4 patients six days after the operation. Other patients had the extraction 7 days after the operation as usual. Each patient showed a favorable progress of healing of the operative wound, and thus the method of this invention proved effective in promoting healing of wounds.

EXPERIMENT 3

The iodine-enriched eggs obtained by the method of Example 1 were given to six boxers, 2 eggs a day, for a period of 105 days during which the boxers had training everyday, and the creatine phosphokinase (CPK) levels in blood before the test and 45 days and 105 days after commencement of the test were measured. The results are shown in Table 3. As obvious from these results, the CPK level in blood which gives a measure of the amount of metabolites in muscle was markedly lowered in each boxer, indicating that the method of this invention using the iodine-enriched egg is helpful in preventing muscular troubles.

TABLE 3

| Boxer No. | CPK level in blood (mU/ml) | | |
|---|---|---|---|
| | before test | 45 days after start of test | 105 days after start of test |
| 1 | 237 | 248 | 123 |
| 2 | 881 | 192 | 100 |
| 3 | 643 | 237 | 111 |
| 4 | 354 | 169 | 166 |
| 5 | 209 | 95 | 155 |
| 6 | 514 | 162 | 82 |
| average | 473 | 183.8 | 122.8 |
| SD | 259.5 | 55.9 | 32.3 |

EXAMPLE 1

In a marketed feed for domestic fowl were mixed calcium iodide of such an amount as to provide an iodine content of 40 ppm in the feed and 2 % of powdered tangle with an iodine content of 2,000 ppm, and the mixed feed was given to hens which had begun to lay eggs three months before. From the seventh day thenceforth after start of feeding with said mixed feed, the hens laid iodine-enriched eggs containing 500 μg of iodine per egg on the average.

EXAMPLE 2

Sodium iodide was added to a marketed fowl feed so that the iodine content in the feed would be 2,500 ppm, and this feed was given to 200 hens which had begun to lay eggs four months before. 200 kg of the obtained iodine-enriched eggs were dried with a spray-dryer to obtain 45 kg of powdered egg containing 360 mg/kg of iodine.

What is claimed is:

1. A method for promoting healing of wounds on the human body and for lowering the amount of creatine phosphokinase in the blood during periods of muscular exercise, which comprises giving a person iodine-enriched egg in an amount effective for promoting healing of the wounds or lowering the amount of creatine phosphokinase in the blood during periods of muscular exercise.

2. The method of claim 1, wherein the amount of the iodine-enriched egg given is selected so that the iodine dose will be about 300 to 4,500 µg per day.

3. The method of claim 2, wherein the iodine dose is about 300 to 1,500 µg per day.

4. The method according to claim 1, wherein the iodine-enriched egg is obtained by giving an iodine-containing material selected from the group consisting of iodine-containing compounds, seaweeds and mixtures thereof to egg-laying hens in excess of their ordinary iodine requirements.

5. The method according to claim 2, wherein the iodine-enriched egg is obtained by giving an iodine-containing material selected from the group consisting of iodine-containing compounds, seaweeds and mixtures thereof to egg-laying hens in excess of their ordinary iodine requirements.

6. The method according to claim 3, wherein the iodine-enriched egg is obtained by giving an iodine-containing material selected from the group consisting of iodine-containing compounds, seaweeds and mixtures thereof to egg-laying hens in excess of their ordinary iodine requirements.

7. The method according to claim 1, wherein the iodine-enriched egg is given in the form of tablet, powder, extract, syrup or emulsion.

8. The method according to claim 2, wherein the iodine-enriched egg is given in the form of tablet, powder, extract, syrup or emulsion.

9. The method according to claim 3, wherein the iodine-enriched egg is given in the form of tablet, powder, extract, syrup or emulsion.

* * * * *